(12) United States Patent
Han et al.

(10) Patent No.: US 11,000,456 B2
(45) Date of Patent: May 11, 2021

(54) COSMETIC MASK KIT PACKED IN BIODEGRADABLE PACKAGING MATERIAL

(71) Applicant: GDK COSMETICS.CO., LTD., Incheon (KR)

(72) Inventors: Hyun-Tak Han, Seoul (KR); Eun-Ji Jang, Seoul (KR)

(73) Assignee: GDK COSMETICS.CO., LTD., Incheon (KR)

( * ) Notice: Subject to any disclaimer, the term of this patent is extended or adjusted under 35 U.S.C. 154(b) by 0 days.

(21) Appl. No.: 16/907,805

(22) Filed: Jun. 22, 2020

(65) Prior Publication Data
US 2020/0397669 A1 Dec. 24, 2020

(30) Foreign Application Priority Data
Jun. 21, 2019 (KR) .................. 10-2019-0074409

(51) Int. Cl.
| | | |
|---|---|---|
| *A61K 8/02* | (2006.01) | |
| *A45D 44/00* | (2006.01) | |
| *A61K 8/06* | (2006.01) | |
| *A61K 8/34* | (2006.01) | |
| *A61K 8/42* | (2006.01) | |
| *A61K 8/92* | (2006.01) | |
| *B65D 65/46* | (2006.01) | |

(52) U.S. Cl.
CPC .......... *A61K 8/0212* (2013.01); *A45D 44/002* (2013.01); *A61K 8/06* (2013.01); *A61K 8/345* (2013.01); *A61K 8/42* (2013.01); *A61K 8/922* (2013.01); *B65D 65/466* (2013.01); *A45D 2200/25* (2013.01)

(58) Field of Classification Search
None
See application file for complete search history.

(56) References Cited

U.S. PATENT DOCUMENTS 8,569,411 B2 * 10/2013 Tilton .................... B32B 9/002
524/425
2006/0182704 A1 8/2006 Gianelli

FOREIGN PATENT DOCUMENTS

| | | |
|---|---|---|
| FR | 3014885 A1 | 6/2015 |
| KR | 10-1199964 B1 | 11/2012 |
| KR | 101199964 B1 * | 11/2012 |
| WO | WO-2017/052192 A1 | 3/2017 |
| WO | WO-2017052192 A1 * | 3/2017 ............... A61K 8/72 |

OTHER PUBLICATIONS

Extended European Search Report from corresponding European Patent Application No. 20181203.9, dated Oct. 23, 2020.

* cited by examiner

*Primary Examiner* — Melissa S Mercier
(74) *Attorney, Agent, or Firm* — Harness, Dickey & Pierce, P.L.C.

(57) ABSTRACT

Disclosed is a cosmetic mask kit packed in a biodegradable packaging material, wherein the use of the mask kit of the present disclosure can be eco-friendly since the mask kit is designed as a 100% biodegradable product, and the mask kit of the present disclosure can significantly improve the satisfaction of a customer since a mask sheet can implement various feelings of use according to the preference of a user.

3 Claims, 11 Drawing Sheets

COSMETIC MASK KIT PACKED IN BIODEGRADABLE PACKAGING MATERIAL

CROSS REFERENCE TO RELATED APPLICATION

This application claims benefit and priority to Korean Patent Application No. 10-2019-0074409 filed on Jun. 21, 2019. The entire disclosures of the application identified in this paragraph is incorporated herein by reference.

FIELD

The present disclosure relates to a cosmetic mask kit packed in a biodegradable packaging material.

BACKGROUND

In recent years, the use of microplastics for cosmetic contents has been prohibited in the cosmetics industry due to environmental pollution and ecological issues caused by plastics. Hence, there is an increasing demand for the development of techniques that reduce or replace the use of plastic materials frequently used in cosmetic containers and packaging materials, and the development of related techniques is also being actively performed.

Sheet-type masks are typically composed of a cosmetic liquid, a mask sheet, and a pouch for packing the same therein. Most of the sheet-type masks are packed in disposable packaging materials for hygiene, preservability, ease of use, and ease of purchase. Therefore, the sheet-type masks usually cause a large amount of trash compared with typical container-type cosmetic products that are used for one to three months after purchase. Meanwhile, typical cosmetic containers are usually made thick in an injection molding manner and can be replaced with glass materials, and biodegradable materials are more easily applied to the cosmetic containers compared with a film form. In a sheet-type mask pouch, an aluminum material is necessarily used in the center of a packaging material to block the moisture evaporation from a cosmetic liquid and prevent the discoloration by light, and a PET material or the like is attached in a film form on the outer surface of a packaging paper to print aesthetic patterns on external appearance of the packaging paper. In addition, an LLDPE material or the like is laminated on the inner surface of an aluminum layer for the binding (sealing) of the pouch and the protection of a cosmetic. While techniques for eco-friendly materials for cosmetic liquids and sheets that constitute current sheet-type masks have been completely developed, alternate techniques for pouches using biodegradable materials that block the evaporation of cosmetic liquids and the discoloration by light have not yet been developed.

SUMMARY

In order to apply a biodegradable material to a packaging material for a mask sheet package, the biodegradable material needs to satisfy the following: (1) the biodegradable material should be processed into a thin film with a thickness of 10-100 micrometers so as to be made into a packaging material; (2) the biodegradable packaging material should have no or little change in properties upon contact with a cosmetic liquid (moisture), leading to no change in quality of the mask sheet package when used; and (3) the biodegradable packaging material should cause no loss of a cosmetic liquid (moisture) or no deterioration of mask sheet contents caused by moisture penetration. The present inventors have conducted intensive and thorough research into development of a mask sheet capable of being packed in a biodegradable packaging material while satisfying the above conditions. As a result, the present inventors have established that the use of a cosmetic in an O/D phase gel type, instead of an existing aqueous cosmetic liquid, causes no loss of the cosmetic and no degradation of cosmetic quality due to a decline in durability of a packaging material, and thus the present inventors have completed the present disclosure. Accordingly, an aspect of the present disclosure is to provide a cosmetic mask kit packed in a biodegradable packaging material.

In accordance with an aspect of the present disclosure, there is provided a cosmetic mask kit packed in a biodegradable packaging material comprising:

a mask sheet; a cosmetic composition in an O/D phase formulation containing a surfactant, a polyol, and oil; and a biodegradable packaging material.

In an embodiment of the present invention, the biodegradable packaging material is selected from the group consisting of poly-hydroxy butyric acid (PHB), polylactic acid (PLA), polybutylene succinate (PBS), poly butylene adipate phthalate (PBAT), polyglycolic acid (PGA), poly (lactic-co-glycolic acid) (PLGA), polycaprolactone (PCL), polydioxanone, polyanhydrides, polycyanoacrylates, polyorthoesters, poly(γ-ethylglutamate), pseudo-poly(amino acids), or a combination thereof, but is not limited thereto.

In the present disclosure, the O/D phase formulation (O/D phase gel or O/D gel) refers to a gel phase obtained by dispersing an oil phase in aggregates of emulsifier molecules. That is, the O/D phase formulation is prepared by adding a large amount of oil to a surfactant (detergent)-containing phase, and thus the O/D phase formulation is in an oil-in-surfactant type. The O/D phase is mixed with water, a polyol, or an aqueous liquid formulation to form a low-viscosity emulsion.

The O/D phase formulation contains: 50-90% of an oil component, irrespective of the type of oil, such as natural oils including olive oil, hydrocarbons, esters, or silicones; 5-50% of a polyol, such as glycerin; 0.1-10% of various surfactant materials, irrespective of the type of surfactant, such as PEG bases, sucrose bases (e.g., sucrose laurate), polyglyceryl bases, microorganism fermentation surfactin (sodium surfactin), or sodium dilauramidoglutamide lysine; and 0-10% of a water component.

In a specific embodiment of the present disclosure, the O/D phase formulation may be composed of, for example: 87 wt % of olive oil, 10 wt % of glycerin, and 3 wt % of sodium dilauramidoglutamide lysine; 79 wt % of olive oil, 1 wt % of glycerin, and 20 wt % of sodium surfactin; or 83 wt % of olive oil, 10 wt % of glycerin, 5 wt % of sucrose laurate, and 2 wt % of purified water, but is not limited thereto.

The cosmetic mask kit of the present disclosure is characterized in that a cosmetic composition in an O/D phase formulation, instead of a typical aqueous cosmetic liquid, is incorporated with the mask sheet. The incorporation may be conducted in the form in which the cosmetic composition in an O/D phase formulation is spread on a portion or the entirety of the surface of the mask sheet.

In an embodiment of the present disclosure, the cosmetic mask kit is characterized in that the mask sheet is applied to the skin of a user after an aqueous cosmetic liquid is added to the cosmetic in an O/D phase formulation to prepare an emulsion.

The cosmetic in an O/D phase formulation causes cloudy whitening (emulsification) immediately and spontaneously when mixed with an aqueous cosmetic liquid containing water or a large amount of moisture. Conventionally, when a sheet-type mask was charged with a cosmetic in an emulsion formulation, an increase in viscosity occurred due to emulsification, resulting in the deterioration in sheet impregnation or the reduction in stability of a formulation caused by a high content of oil. As a result, the cosmetic applied to a sheet-type mask typically contained less than 5% of an oil component.

However, in the cosmetic mask kit of the present disclosure, the cosmetic composition in an O/D phase gel formulation, instead of a typical aqueous cosmetic composition, is incorporated with the mask sheet, and therefore, the components of the aqueous cosmetic or the contents thereof may be controlled according to the preference of a user.

Therefore, a mask sheet containing an oil component in various ranges of 1-90% can be designed, and the components of the aqueous cosmetic and the contents thereof can be variously controlled to implement various feelings of use, leading to an improvement in customer satisfaction through semi-customized products.

In another embodiment of the present disclosure, the cosmetic mask kit of the present disclosure may be provided such that the cosmetic mask kit further includes an aqueous cosmetic, selected according to the preference of a user, in a separate package.

In addition, in still another embodiment of the present disclosure, the cosmetic mask kit of the present disclosure may be provided such that the cosmetic mask kit further includes an aqueous cosmetic in a separate compartment inside the packaging paper. The shape and size of the compartment is not limited.

In accordance with an aspect of the present disclosure, there is provided a method for using a mask sheet, the method including:

(a) opening a packaging paper from the above-described cosmetic mask kit packed in a biodegradable packaging material;

(b) adding an aqueous cosmetic liquid inside the packaging paper of the cosmetic mask kit;

(c) mixing the mask sheet, the cosmetic composition in an O/D phase formulation, and the added aqueous cosmetic liquid; and (d) taking out the mask sheet from the packaging paper and contacting the mask sheet with the skin of a user.

In an embodiment of the present disclosure, the opening of the packaging paper in step (a) is performed in order to add the aqueous cosmetic liquid inside the packaging paper in step (b), which is the next step, and the opening of the packaging paper means for example cutting or tearing one end portion of the packaging paper. In step (a), only a portion of the packaging paper is removed and the packaging paper is made into a container shape, and the reason is that even after the packaging paper is opened, the packaging paper needs to be opened so as to accommodate the cosmetic liquid added in step (b) for a predetermined time.

In an embodiment of the present disclosure, the aqueous cosmetic liquid in step (b) is selected according to the preference of a user, and thus i) the aqueous cosmetic liquid may be prepared by a user; ii) the aqueous cosmetic liquid may be provided in a separate package from the cosmetic mask kit; or iii) the aqueous cosmetic liquid may be contained in a separate compartment inside the packaging paper of the cosmetic mask kit. When the aqueous cosmetic liquid is contained in the separate compartment inside the packaging paper of the cosmetic mask kit iii), the above step includes breaking the boundary of the separate compartment inside the packaging paper of the cosmetic mask kit.

In an embodiment of the present disclosure, the mixing in step (c) is a step where the cosmetic in an O/D phase is mixed with the aqueous cosmetic liquid to prepare an emulsion and the mask sheet is uniformly wetted in the prepared emulsion. The time and degree of the mixing are sufficient as long as the cosmetic in an O/D phase accommodated in the packaging paper is uniformly mixed with the aqueous cosmetic liquid and the mask sheet can be so sufficiently wetted in the aqueous cosmetic liquid as to be suitable for use, but is not particularly limited thereto.

In an embodiment of the present disclosure, step (d) is a step where a user takes out the mask sheet from the mask sheet of the present disclosure and contacts the mask sheet with the skin. The time for contact can be controlled according to the preference of the user, but is not particularly limited thereto.

The cosmetic mask kit of the present disclosure includes a small amount of a cosmetic in an O/D phase gel formulation, instead of a large volume of typical aqueous cosmetic composition, leading to a decrease in packaging size, thereby reducing the resource usage, improving distribution efficiency, and making it easy for customers to carry (improved portability).

As validated in the examples of the present disclosure, the aqueous cosmetic, upon the contact with a biodegradable pouch, significantly reduces the tensile strength of the biodegradable pouch, but the cosmetic in an O/D phase formulation, instead of the aqueous cosmetic, with which the pouch is charged, does not affect the tensile strength of the biodegradable pouch, so that product preservability and formulation stability can be ensured even when only a biodegradable packaging material is used for packing without the use of either an aluminum material or a non-biodegradable packaging material.

Therefore, the cosmetic mask kit of the present disclosure can provide 100% biodegradable products by including a biodegradable packaging material, a biodegradable mask sheet, and a biodegradable cosmetic composition.

According to the present disclosure, the present disclosure provides a mask sheet packed in a biodegradable packaging material. The use of the mask sheet of the present disclosure can be eco-friendly since the mask sheet is designed as a 100% biodegradable product, and the mask sheet of the present disclosure can significantly improve the satisfaction of a customer since the mask sheet can implement various feelings of use according to the preference of a user.

DETAILED DESCRIPTION

Hereinafter, the present disclosure will be described in more detail with reference to examples. These examples are only for illustrating the present disclosure more specifically, and it would be apparent to those skilled in the art that the scope of the present disclosure is not limited by these examples according to the gist of the present disclosure.

EXAMPLES

Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

Example 1: Emulsification of Cosmetic in O/D Phase

In order to investigate properties and states of an O/D gel of the present disclosure before and after the addition of an aqueous cosmetic liquid, the aqueous cosmetic liquid was added to the O/D gel. The images before, during, and after the addition are shown in FIGS. 1A to 1C and 2. The composition of the O/D gel of the present disclosure is shown in Table 1 below.

TABLE 1

| O/D phase | Content (wt %) |
| --- | --- |
| Glycerin (polyol) | 10 |
| Sodium dilauramidoglutamide lysine | 3 |
| Olive oil (oil) | 87 |

Figure 1A:
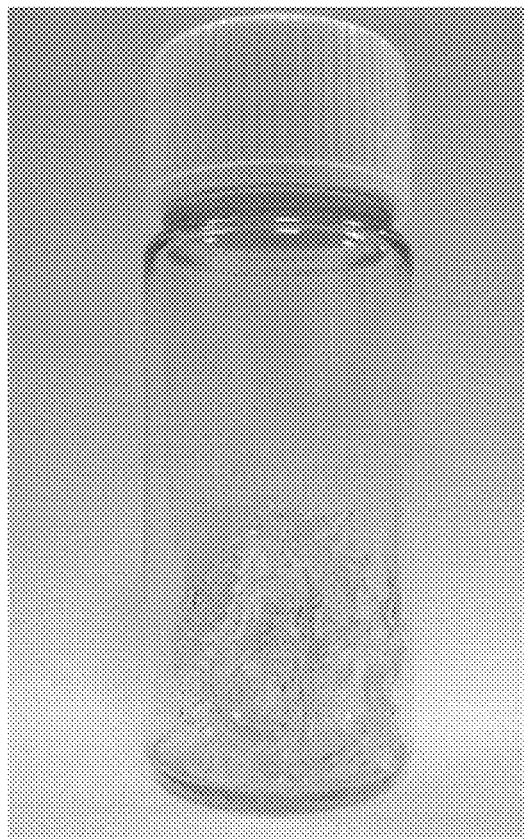
FIGS. 1A, 1B and 1C show a cosmetic in an O/D phase formulation, which is a component of a mask sheet of the present disclosure, before, during, and after the mixing with an aqueous cosmetic liquid.
Figure 1B:
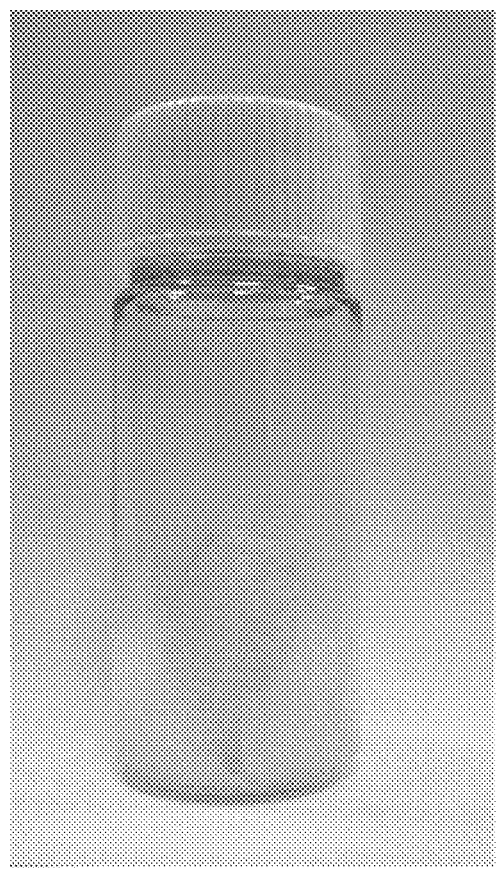
Figure 1C:
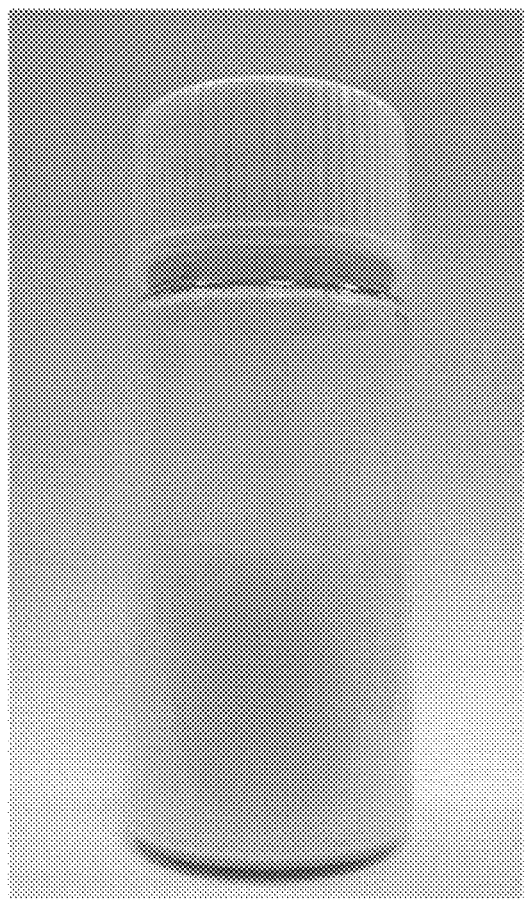
Figure 2:
FIG. 2 shows a cosmetic in an O/D phase formulation, which is a component of a mask sheet of the present disclosure, before (left) and after (right) mixing with an aqueous cosmetic liquid.

As shown in FIG. 1A and the left panel of FIG. 2, the cosmetic in an O/D phase gel type before the addition of the aqueous cosmetic liquid had the same properties and states as a gel. As shown in FIGS. 1B and 1C and the right panel of FIG. 2, the O/D gel became an emulsion form by emulsification immediately when the aqueous cosmetic liquid was added thereto.

Example 2: Test of Volatility According to Packaging Material and Cosmetic Formulation (Aqueous Phase or O/D Phase In order to investigate volatility of a cosmetic according to the packaging material and the formulation of the cosmetic packed in the packaging material, the following test was conducted.

As for the packaging material, a biodegradable pouch, a vinyl pouch, and an alumina pouch were used. Specifically, a pouch (80 μm) of a composite material obtained by binding poly lactic acid (PLA)/polybutylene (PBS)/PBAT was used as a biodegradable pouch; a composite material obtained by binding polyethylene terephthalate (PET)/NYLON/linear low-density polyethylene (LLDPE) was used as a vinyl pouch; and a pouch obtained by binding polyethylene terephthalate (PET, 12 μm)/Aluminum (6 μm)/linear low-density polyethylene (LLDPE, 80 μm) from the outside was used as an aluminum pouch.

As for the formulation of a cosmetic, an aqueous cosmetic and a cosmetic in an O/D phase were used. Under conditions of 45° C. and room temperature (RT), 20 g of the aqueous cosmetic was introduced and 1 g of the cosmetic in an O/D phase was introduced for each packaging material, and after 6 hours, 12 hours, 24 hours, and 36 hours, weight measurement was conducted.

The results relevant to the aqueous cosmetic are shown in Table 2, and the results relevant to the cosmetic in an O/D phase are shown in Table 3.

TABLE 2

Test results of volatility with temperature and over time after application of 20 g of cosmetic liquid in biodegradable pouch, vinyl pouch, and aluminum pouch

| | | Time | | | |
| --- | --- | --- | --- | --- | --- |
| Temperature | Material | 6 h | 12 h | 24 h | 36 h |
| RT | Biodegradable pouch | −0.45 g | −0.60 g | −1.03 g | −1.73 g |
| | Vinyl pouch | −0.02 g | −0.03 g | −0.05 g | −0.07 g |
| | Aluminum pouch | 0 g | 0 g | 0 g | 0 g |
| 45° C. | Biodegradable pouch | −0.60 g | −1.35 g | −2.06 g | −2.51 g |
| | Vinyl pouch | −0.20 g | −0.28 g | −0.32 g | −0.35 g |
| | Aluminum pouch | 0 g | 0 g | 0 g | 0 g |

TABLE 3

Test results of volatility with temperature and over time after
application of O/D gel in biodegradable pouch

| Temperature | Time | | | |
| --- | --- | --- | --- | --- |
| | 6 h | 12 h | 24 h | 36 h |
| RT | 0 g | 0 g | 0 g | 0 g |
| 45° C. | 0 g | 0 g | 0 g | 0 g |

The volatility test was conducted in conditions of RT and 45° C. for the biodegradable pouch, vinyl pouch, and aluminum pouch each charged with 20 g of the aqueous cosmetic liquid. As a result, as shown in Table 2, the extent of volatility was in the order of biodegradable pouch>vinyl pouch>aluminum pouch. Meanwhile, there were no changes in volatility with temperature and over time when a dry-type O/D gel was applied to the biodegradable pouch.

It was therefore verified that a typical cosmetic in an aqueous formulation had problems in preservability and distribution safety, resulting from volatility or the like, and thus was not suitable to pack in a biodegradable pouch. However, it was verified that the cosmetic in an O/D phase gel formulation had no problem in preservability and distribution safety even when packed in a biodegradable pouch having highest volatility.

However, the biodegradable packaging paper can be subjected to printing in a limited manner. Therefore, in order to apply various printing manners, such as laser printing, and UV printing, or to improve printing quality, a paper needs to be bound to the biodegradable pouch. When the biodegradable pouch, of which applicability was confirmed in Table 3, was bound to a paper to manufacture a packaging paper composed of poly lactic acid (PLA)/polybutylene (PBS)/PBAT/paper and an O/D phase gel or an aqueous cosmetic liquid was actually packed in the packaging paper, it was investigated whether the packaging paper was damaged by the cosmetic packed in the packaging paper according to the temperature and time.

The test was conducted in the same manner as the above-described method, and the external appearance of the packaging paper was photographed before 0/D gel packaging and 36 hours after 0/D gel packaging. The results are shown in Table 4 and FIG. 3.

TABLE 4

Test results of volatility with temperature and
over time after application of O/D gel to packaging
paper having bound biodegradable pouch/paper

| Temperature | Time | | | |
| --- | --- | --- | --- | --- |
| | 6 h | 12 h | 24 h | 36 h |
| RT | 0 g | 0 g | 0 g | 0 g |
| 50° C. | 0 g | 0 g | 0 g | 0 g |

Figure 3A:
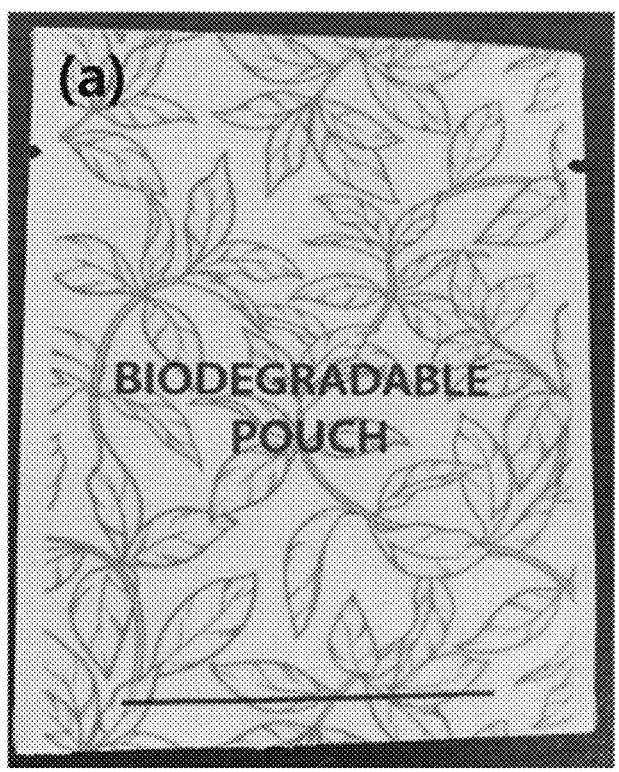
FIGS. 3A and 3B show the external appearance of a packaging paper in which a paper was bound to a biodegradable pouch corresponding to a packaging material for a mask sheet of the present disclosure, before (a) and 36 hours after (b) a cosmetic in an O/D phase formulation was packed in the packaging paper.
Figure 3B:
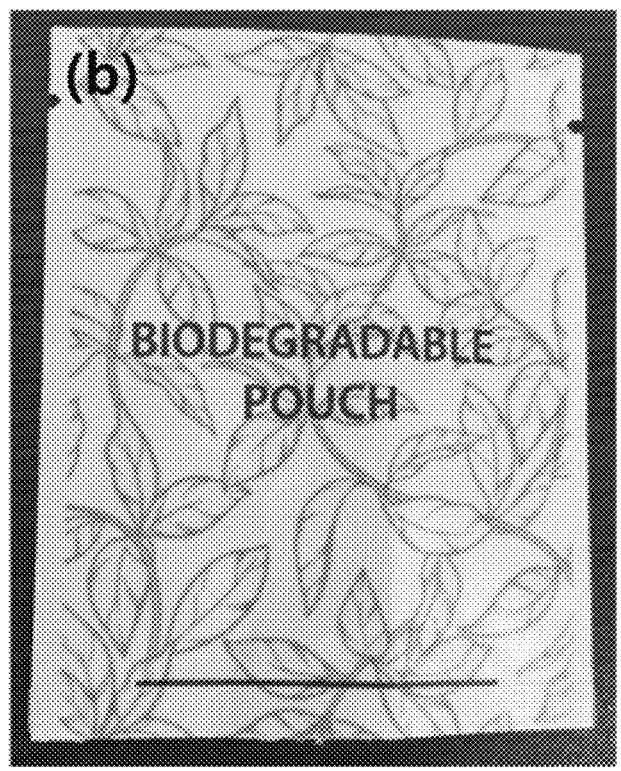

As shown in Table 4, as for the packaging paper in which a paper was bound to the biodegradable packaging material of the present disclosure, the cosmetic in an O/D phase gel formulation showed no change in weight, indicating no volatility. As shown in FIG. 3, even after the cosmetic in an O/D phase gel formulation was packed, there was no change in printing quality or external appearance of the packaging paper, indicating no damage resulting from the cosmetic.

Figure 4A:
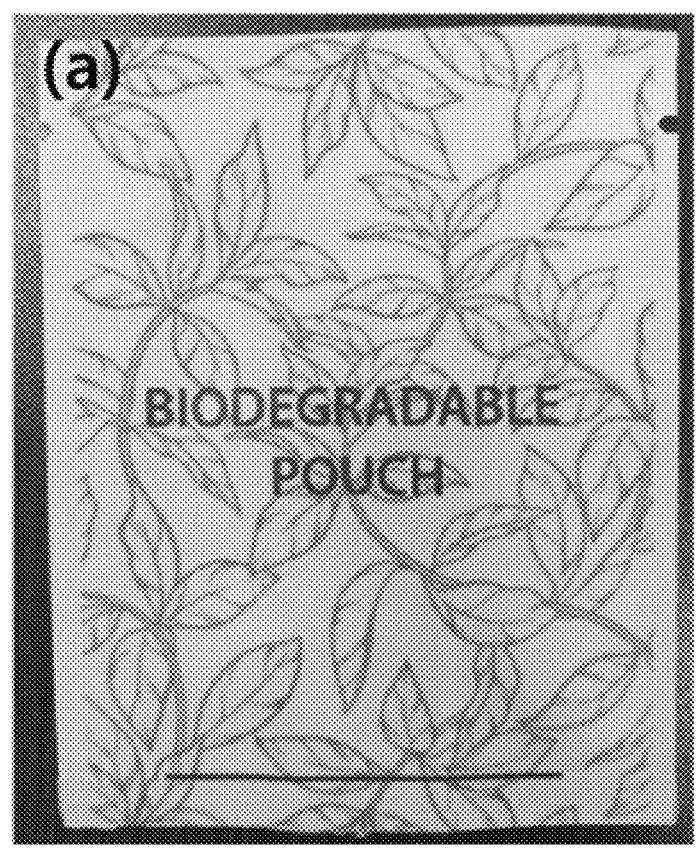
FIGS. 4A and 4B compares the external appearance of a packaging paper in which a paper was bound to a biodegradable pouch corresponding to a packaging material for a mask sheet of the present disclosure before (a) and 36 hours after (b) an aqueous cosmetic was packed in the packaging paper.
Figure 4B:

In order to investigate the durability of the packaging paper, in which a paper was bound to the biodegradable packaging material of the present disclosure, when a typical aqueous cosmetic liquid instead of an O/D gel was packed, the external appearance of the packaging paper where a paper was bound to the biodegradable packaging material of the present disclosure was photographed before ((a) of FIG. 4) and 36 hours after ((b) of FIG. 4) the aqueous cosmetic liquid was packed in the packaging paper. The results are shown FIG. 4. As shown in (b) of FIG. 4, when the aqueous cosmetic was packed in the packaging paper, the packaging paper was easily wet and the printing of the packaging paper was easily damaged even by weak scrape or friction. Therefore, in cases where the biodegradable packaging material of the present disclosure is used for packaging mask sheet, it is preferable that a cosmetic in an O/D phase gel formulation, instead of a typical aqueous cosmetic, is accommodated in the biodegradable packaging material.

Example 3: Change in Tensile Strength of
Biodegradable Pouch According to Formulation of
Cosmetic 3-1. Tensile Strength Test 1

In order to investigate whether a biodegradable pouch was degraded according to the formulation of a cosmetic, biodegradable pouches in which an aqueous cosmetic liquid (20 g) and an O/D phase gel (1 g) had been respectively preserved at 45° C. for 36 hours were cut into the same size (6 cm), and the pouch cuts were pulled to both sides while both lines were aligned, thereby examining the extent of stretching (A: biodegradable pouch to which cosmetic liquid had been applied, B: biodegradable pouch to which a cosmetic in an O/D phase gel formulation had been applied, C: biodegradable pouch to which cosmetic liquid had not been applied).

Figure 5A:
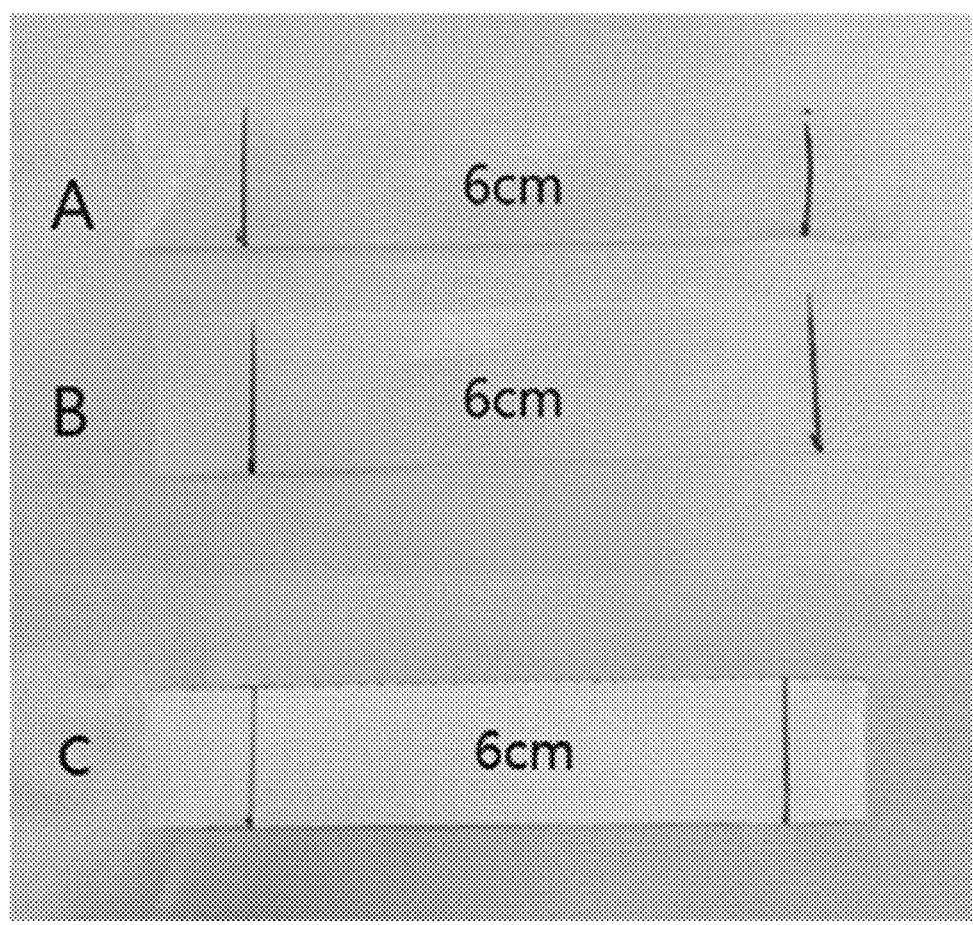
FIGS. 5A and 5B compare the tensile strength test results of biodegradable pouches corresponding to a packaging material of a mask sheet of the present disclosure when (A) a typical aqueous cosmetic and (B) a cosmetic in an O/D phase formulation were in contact with the biodegradable pouches, respectively.
Figure 5B:
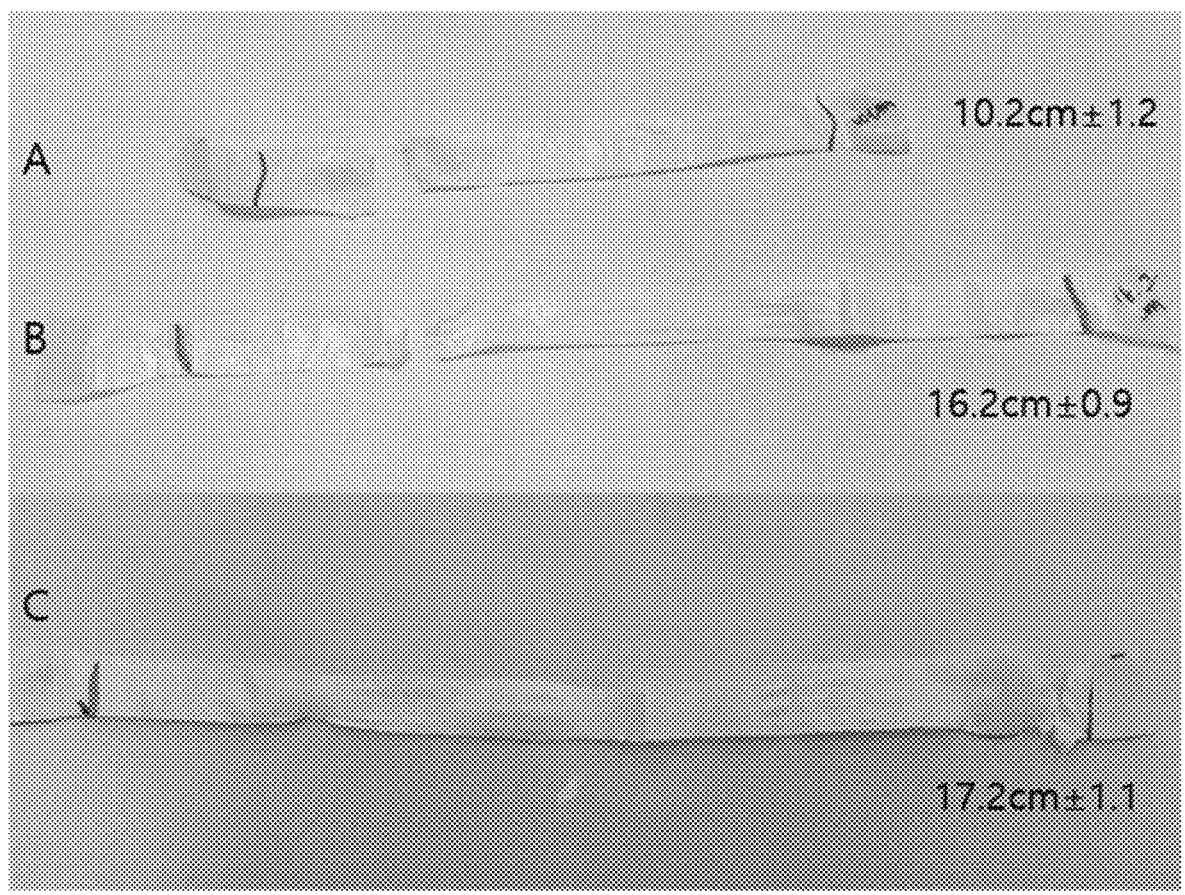

The results are shown in FIGS. 5A and 5B. As a result of testing the tensile strength by pulling the pouch cuts to both sides while both lines were aligned, the biodegradable pouch to which the aqueous cosmetic liquid had been applied showed a decline in durableness, indicating a reduction in pouch tensile strength, compared with the biodegradable pouch to which the cosmetic in an O/D gel formulation had been applied and the existing biodegradable pouch to which a cosmetic liquid had not been applied.

3-2. Tensile Strength Test 2

In order to quantitatively measure the change in tensile strength of biodegradable pouches in the same conditions as in 3-1 above, the tensile strength was measured for 1) a biodegradable pouch charged with an aqueous cosmetic liquid at 45° C. and 2) a biodegradable pouch charged with a cosmetic in an O/D phase gel type in conditions of a speed of 100 mm/min and a height of 500% by using a tensile strength measurement device MultlTest2.5-i after 7 days at 45° C.

The results are shown in Table 5.

TABLE 5

| Classification | Elongation rate |
| --- | --- |
| 1 | 251.65% |
| 2 | 401.45% |

** Elongation rate: the stretching rate of material in tensile test

As shown in Table 5, from the biodegradable pouch tensile test results, the biodegradable pouch charged with the aqueous cosmetic liquid 1) showed a lower elongation compared with the biodegradable pouch charged with the O/D phase formulation 2). It was therefore confirmed that the cosmetic in an O/D phase formulation of the present disclosure is applicable to a biodegradable pouch.

Example 4: Change in Tearability of Biodegradable Pouch According to Formulation of Cosmetic In order to investigate whether a biodegradable pouch was degraded according to the formulation of a cosmetic, an aqueous cosmetic liquid (20 g) and an O/D phase gel (1 g) was preserved at 45° C. for 3 days in biodegradable pouches and the upper ends of the biodegradable pouches were torn, and then tearing surfaces thereof were observed.

Figure 6A:
FIGS. 6A and 6B compare tearing surfaces of packaging materials after (A) a typical aqueous cosmetic and (B) a cosmetic in an O/D phase formulation were in contact with biodegradable pouches corresponding to a packaging material of a mask sheet of the present disclosure.
Figure 6B:

As shown in FIGS. 6A and 6B, in the biodegradable pouch in which the aqueous cosmetic liquid had been contained, the surface thereof was degraded to be crumpled by the aqueous cosmetic liquid and the tearing surface along the tearing line was stretched.

What is claimed is:

1. A method for using a mask sheet, the method comprising:
   (a) removing a portion of a packaging paper from a cosmetic mask kit packed in a biodegradable packaging material;
   (b) adding an aqueous cosmetic liquid inside the packaging paper of the cosmetic mask kit;
   (c) mixing the mask sheet, the cosmetic composition in an oil in surfactant emulsion gel, and the added aqueous cosmetic liquid; and
   (d) taking out the mask sheet from the packaging paper and contacting the mask sheet with the skin of a user.

2. The method of claim 1, wherein the biodegradable packaging material is selected from the group consisting of poly-hydroxy butyric acid (PHB), polylactic acid (PLA), polybutylene succinate (PBS), poly butylene adipate phthalate (PBAT), polyglycolic acid (PGA), poly(lactic-co-glycolic acid) (PLGA), polycaprolactone (PCL), polydioxanone, polyanhydrides, polycyanoacrylates, polyorthoesters, poly(γ-ethylglutamate), pseudo-poly(amino acids), or a composite material thereof.

3. The method of claim 1, wherein the kit further comprises an aqueous cosmetic in a separate package, the aqueous cosmetic being selected according to the preference of the user.

* * * * *